United States Patent [19]

Roos et al.

[11] 4,130,558

[45] Dec. 19, 1978

[54] PROCESS FOR PREPARATION OF ALKALI METAL SALTS OF AMPICILLIN

[75] Inventors: Otto Roos, Ingelheim am Rhein; Dieter Essig, Bad Kreuznach, both of Germany

[73] Assignee: Boehringer Ingelheim GmbH, Ingelheim am Rhein, Germany

[21] Appl. No.: 797,928

[22] Filed: May 18, 1977

[30] Foreign Application Priority Data

May 28, 1976 [DE] Fed. Rep. of Germany ....... 2623835

[51] Int. Cl.$^2$ ........................................... C07D 499/68
[52] U.S. Cl. ................................................. 260/239.1
[58] Field of Search ...................... 260/239.1; 424/271

[56] References Cited

U.S. PATENT DOCUMENTS 4,029,804  6/1977  Clark et al. ........................ 424/271

OTHER PUBLICATIONS

Kirk–Othmer, Encyclopedia of Chemical Technology, 2nd ed. pp. 368–369 (1965).

*Primary Examiner*—Gerald A. Schwartz
*Attorney, Agent, or Firm*—Hammond & Littell

[57] ABSTRACT

A process for the preparation of an alkali metal salt of ampicillin, especially the sodium salt, which comprises adding to an aqueous suspension of ampicillin, at a temperature not exceeding about 4° C, an aqueous solution of an equimolar or somewhat lesser amount of an alkali metal base, filtering the resulting solution until sterile, freezing the filtrate, and lyophilizing the frozen filtrate.

2 Claims, No Drawings

PROCESS FOR PREPARATION OF ALKALI METAL SALTS OF AMPICILLIN

This invention relates to a novel process for the preparation of alkali metal salts of ampicillin, particularly the sodium salt, by freeze-drying.

BACKGROUND OF THE INVENTION AND THE PRIOR ART

German Pat. No. 1,197,460 discloses a process for the preparation of very pure salts of ampicillin which comprises reacting crude ampicillin with a trialkylamine in an organic solvent to form the corresponding ammonium salt of ampiillin and, after separating impurities, precipitating the alkali metal salt of ampicillin by further reaction with an alkali metal salt of a carboxylic acid.

The said German Patent teaches, inter alia, that aqueous solutions of salts of ampicillin, which may be prepared by dissolving ampicillin in an aqueous solution of the calculated amount of sodium bicarbonate for example, are not very stable; upon evaporation of such solutions, even under the most gentle conditions such as in the rotary evaporator or by freeze-drying, about half of the ampicillin in the recovered salt has been destroyed. Therefore, it does not appear to be possible to isolate salts of ampicillin from aqueous solutions without significant decomposition of the ampicillin.

The belief that salts of ampicillin cannot be isolated from aqueous solutions without substantial decomposition of the ampicillin has heretofore to our knowledge never been put in doubt. Accordingly, subsequent prior publications such as German Offenlegungsschrift Nos. 1,670,111, 1,670, 191, 1,795,129 and 1,903,388 always disclose the same basic process, that is, the double decomposition of ammonium salts of ampicillin in organic solvents, as the only useful method for the preparation of alkali metal salts of ampicillin.

OBJECTS OF THE INVENTION

It is an object of the present invention to provide a process for the preparation of alkali metal salts of ampicillin in aqueous solution without significant loss of the active ampicillin component.

Other objects and advantages of the invention will become apparent as the description thereof proceeds.

DESCRIPTION OF THE INVENTION

We have discovered that alkali metal salts of ampicillin, especially sodium ampicillin, can after all be prepared in aqueous solution by lyophilization, and that the ampicillin salts thus obtained have the same biological efficacy and the same stability as the analogous ampicillin salts prepared by the methods disclosed in the prior art.

The process for the preparation of alkali metal salts of ampicillin, especially of sodium ampicillin, pursuant to the present invention comprises the steps of adding to an aqueous suspension of ampicillin at a temperature not exceeding about 4° C. an aqueous solution of an equimolar amount or up to 10% less than the equimolar amount of an alkali metal base in a manner such that no local over-alkalization occurs, sterile-filtering the resulting solution without delay, immediately freezing the filtrate and lyophilizing the frozen filtrate.

A significant decomposition of the active substance can be avoided in the process of the present invention by taking care that during the addition of the aqueous alkali metal base solution to the aqueous ampicillin suspension the temperature of the latter be kept as low as possible, the addition of the alkali metal base solution be controlled so that no local over-alkalization occurs, and the sterile-filtered filtrate is immediately frozen for the subsequent lyophilization step.

The upper temperature limit at which the ampicillin suspension should be maintained during the addition of the alkali metal base solution is about +4° C., but it is more advantageous to work at a temperature around 0° C. or less, provided the aqueous medium remains liquid and does not begin to freeze. Local over-alkalization and thus the presence of substantial amounts of unreacted alkali metal base can be avoided by continuously and intensively stirring the aqueous mixture. The aqueous alkali metal base solution is advantageously also cooled to between 0° and 4° C. before it is added to the ampicillin suspension.

The ampicillin used in the process of the instant invention may be racemic ampicillin or an epimer thereof, preferably D-(−)-ampicillin, and may be employed in anhydrous as well as in hydrate form.

Based on stability tests with aqueous sodium ampicillin solutions in the liquid and frozen state, we have found that sodium ampicillin in aqueous solution at 0° to 4° C. does not undergo discernable decomposition until after several hours, and the salt solution in the frozen state, for instance at −40° C., remains practically completely stable for more than two days. As far as the successful salt formation and its isolation in the present process are concerned, these findings mean that the conditions favoring stability of the ampicillin salt must be maintained while the salt is in aqueous solution and that this is the critical phase of the process sequence. The elapsed time, beginning with the addition of the alkali metal base solution to the aqueous ampicillin suspension and extending through the completion of the freezing procedure prior to lyophilization, should not exceed three hours and should preferably be about two hours. Once the sodium ampicillin solution has been frozen it can then be freeze-dried without undue haste within the conventional time period required for lyophilization, since we have ascertained that ampicillin undergoes no decomposition whatever during the lyophilization procedure. In fact, even after repeated freeze-drying of one and the same sample alternated with redissolution of the freeze-dried product in water and immediate freezing of the solution, no significant loss in biological efficacy could be observed.

The process of the present invention can be used to prepare all alkali metal salts of ampicillin. For the salt formation the conventional alkali metal bases or basic alkali metal salts such as alkali metal hydroxides, bicarbonates or carbonates, but preferably sodium hydroxide, sodium bicarbonate or sodium carbonate, can be employed. Although it is conventional to use an equimolar amount of the alkali metal base for the salt formation, the process of the present invention can be carried out with up to 10% less than the equimolar amount based on the molar quantity of ampicillin. The lyophilizate obtained by the process of the instant invention is readily water-soluble under standard conditions.

After undergoing the freeze-drying treatment, the alkali metal salt of ampicillin thus obtained still contains about 1.5% water as residual moisture, which can be reduced by extending the lyophilization time or by subsequently drying the freeze-dried product, for instance in vacuo over phosphorus pentoxide. After a storage period of three months at 25° C., a sample of sodium ampicillin prepared by the process of this invention and having a residual moisture content of 1.5% by weight showed no evidence of decomposition.

Alkali metal salts of ampicillin are useful for the treatment of all infections for which a corresponding therapy is indicated and where parenteral administration of the therapeutic agent is unavoidable.

The following examples illustrate the present invention and will enable others skilled in the art to understand it more completely. It should be understood, however, that the invention is not limited solely to the particular examples given below.

EXAMPLE 1

6 ml of an aqueous 1N sodium hydroxide solution (6 millimols of NaOH) which had been cooled to about 0° C. was added dropwise over a period of 5 minutes to a suspension of 2.42 gm (6 millimols) of ampicillin trihydrate in 24 ml of water at about 0° C., while cooling and vigorously stirring. The resulting clear solution was immediately sterile-filtered, that is, filtered to remove suspended particles, and the filtrate was without delay frozen in bulk by the shell-freezing process. Thereafter, the frozen filtrate was lyophilized, yielding 2.2 gm of white sodium ampicillin having a residual moisture content of 1.35% by weight and a microbiological activity of 94% (U.S.P. standard).

Based on ampicillin content determinations and stability tests of the lyophilized sodium ampicillin, which were made
- (a) I.R. - spectroscopically by measurement of the extinction of the $\beta$-lactam absorption band at 1770 $cm^{-1}$ (5.65 $\mu$) in KBr,
- (b) microbiologically, based on U. S. P. standard, and
- (c) iodometrically, practically no decrease in activity was found over the starting ampicillin and a commercial sodium ampicillin product (Binotal ®).

In order to determine the storage stability of the sodium ampicillin obtained in this example, the end product was filled into injection ampules, the ampules were closed with rubber stoppers, aluminum foil caps were placed over the stoppers, and the ampules were stored for three months at +25° C. No decrease in activity could be discerned over the pre-storage values.

EXAMPLE 2

A suspension of 24.18 gm (60 millimols) of ampicillin trihydrate in 140 ml of water was admixed with 55.2 ml of an aqueous 1N sodium hydroxide solution (8% less than equimolar amount of NaOH) in the manner and under the conditions described in Example 1, and the sodium ampicillin was isolated in exactly the same manner as in Example 1.

The lyophilizate was tested for ampicillin content and stability by the methods indicated in Example 1. The microbiological test showed a 92% content of active substance (U.S.P. standard).

EXAMPLE 3

A suspension of 2.418 kg (6 mols) of ampicillin trihydrate in 15 liters of water was admixed with 300 ml of 2N sodium hydroxide, and the sodium ampicillin was isolated as a snow-white powder by lyophilization in the same manner and under the exact same conditions as in Example 1. The product was storage-stable and showed an active substance content of 91.5% in the microbiological test and 92.7% in the iodometric test.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We Claim:

1. The method of preparing an alkali metal salt of ampicillin, which comprises the steps of adding to a liquid aqueous suspension of ampicillin at a temperature not exceeding about 4° C. an aqueous solution of an equimolar amount or up to 10% less than an equimolar amount, based on the ampicillin, of an alkali metal base or basic alkali metal salt, while avoiding local over-alkalization in the suspension, immediately sterile-filtering the resulting aqueous solution, immediately freezing the filtrate, and lyophilizing the frozen filtrate.

2. The method of claim 1, where the said aqueous solution which is added to the ampicillin suspension is aqueous sodium hydroxide.

* * * * *